US012653496B2

(12) United States Patent
Butler et al.

(10) Patent No.: US 12,653,496 B2
(45) Date of Patent: Jun. 16, 2026

(54) INTRAVASCULAR IMAGING CATHETER

(71) Applicant: Boston Scientific Scimed, Inc., Maple Grove, MN (US)

(72) Inventors: Quinn Mackenzie Butler, Minneapolis, MN (US); Jeffrey Steven Fuller, Brooklyn Park, MN (US); Andrew Strom, Golden Valley, MN (US); Bryan Joseph Plunger, Shoreview, MN (US); Joseph Alan Kronstedt, New Hope, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/975,086

(22) Filed: Dec. 10, 2024

(65) Prior Publication Data

US 2025/0186019 A1    Jun. 12, 2025

Related U.S. Application Data

(60) Provisional application No. 63/608,447, filed on Dec. 11, 2023.

(51) Int. Cl.
*A61B 8/00*        (2006.01)
*A61B 5/00*        (2006.01)
*A61B 8/12*        (2006.01)

(52) U.S. Cl.
CPC .............. *A61B 8/12* (2013.01); *A61B 5/0066* (2013.01); *A61B 5/6852* (2013.01); *A61B 8/445* (2013.01)

(58) Field of Classification Search
CPC ......... A61B 8/12; A61B 8/445; A61B 5/0066; A61B 5/6852
See application file for complete search history.

(56) References Cited

U.S. PATENT DOCUMENTS 5,772,609 A    6/1998  Nguyen et al.
6,139,510 A    10/2000 Palermo
(Continued)

FOREIGN PATENT DOCUMENTS

EP        2844135 B1    6/2022

OTHER PUBLICATIONS

International Search Report and Written Opinion dated Feb. 28, 2025 for International Application No. PCT/US2024/059295.
(Continued)

*Primary Examiner* — Joel F Brutus
(74) *Attorney, Agent, or Firm* — Seager, Tufte & Wickhem, LLP

(57)        ABSTRACT

Intravascular imaging devices as well as methods for making and using intravascular imaging devices are disclosed. An intravascular imaging device may include a catheter shaft including a hypotube region, an imaging window region, and a distal end region having a guidewire lumen formed therein. The hypotube region may include a first portion free of slots and a second portion having a plurality of slots formed therein. At least a reduced diameter section of the second portion of the hypotube region may have an outer diameter that is less than an outer diameter of the first portion of the hypotube region. The imaging window region may be coupled to the reduced diameter section of the second portion of the hypotube region. An imaging core may be disposed within the catheter shaft.

20 Claims, 6 Drawing Sheets

(56) References Cited

U.S. PATENT DOCUMENTS

| | | | |
|---|---|---|---|
| 8,728,010 B2 | 5/2014 | Hirshman | |
| 9,474,506 B2 | 10/2016 | Magnin et al. | |
| 2004/0181174 A2 | 9/2004 | Davis et al. | |
| 2005/0215942 A1 | 9/2005 | Abrahamson et al. | |
| 2007/0066900 A1 | 3/2007 | O'Keeffe | |
| 2012/0059241 A1 | 3/2012 | Hastings et al. | |
| 2014/0171804 A1 | 6/2014 | Van Hoven | |
| 2014/0180031 A1 | 6/2014 | Anderson | |
| 2014/0180122 A1 | 6/2014 | Stigall et al. | |
| 2014/0276109 A1 | 9/2014 | Gregorich | |
| 2017/0164925 A1 | 6/2017 | Marshall et al. | |
| 2022/0040454 A1* | 2/2022 | Hamm .............. | A61M 25/0158 |
| 2022/0142462 A1 | 5/2022 | Douk et al. | |

OTHER PUBLICATIONS

International Search Report and Written Opinion for International Application No. PCT/US2024/017209, dated Jun. 11, 2024. (12 pages).

\* cited by examiner

INTRAVASCULAR IMAGING CATHETER

CROSS-REFERENCE TO RELATED APPLICATIONS

This application claims the benefit of priority under 35 U.S.C. § 119 of U.S. Provisional Application No. 63/608, 447, filed Dec. 11, 2023, the entire disclosure of which is hereby incorporated by reference.

TECHNICAL FIELD

The present disclosure pertains to medical devices, and methods for manufacturing medical devices. More particularly, the present disclosure pertains to intravascular imaging catheters.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An intravascular imaging device is disclosed. The intravascular imaging device comprises: a catheter shaft including a hypotube region, an imaging window region, and a distal end region having a guidewire lumen formed therein; wherein the hypotube region includes a first portion free of slots and a second portion having a plurality of slots formed therein; wherein at least a reduced diameter section of the second portion of the hypotube region has an outer diameter that is less than an outer diameter of the first portion of the hypotube region; wherein the imaging window region is coupled to the reduced diameter section of the second portion of the hypotube region; and an imaging core disposed within the catheter shaft.

Alternatively or additionally to any of the embodiments above, the imaging core is translatable within the catheter shaft.

Alternatively or additionally to any of the embodiments above, the imaging core includes an ultrasound transducer.

Alternatively or additionally to any of the embodiments above, the imaging core includes an optical coherence tomography imaging device.

Alternatively or additionally to any of the embodiments above, the reduced diameter section extends along substantially the full length of the second portion of the hypotube region.

Alternatively or additionally to any of the embodiments above, the reduced diameter section extends along only a distal section of the second portion of the hypotube region.

Alternatively or additionally to any of the embodiments above, the second portion of the hypotube region includes a proximal section having an outer diameter that is substantially equal to the outer diameter of the first portion of the hypotube region.

Alternatively or additionally to any of the embodiments above, the imaging window region includes a distal portion having a first outer diameter and a proximal portion having a second outer diameter greater than the first outer diameter.

Alternatively or additionally to any of the embodiments above, the proximal portion of the imaging window region is disposed along the reduced diameter section of the second portion of the hypotube region.

Alternatively or additionally to any of the embodiments above, further comprising a sleeve disposed along the reduced diameter section of the proximal portion of the imaging window region.

Alternatively or additionally to any of the embodiments above, further comprising a sleeve disposed along the second portion of the hypotube region.

Alternatively or additionally to any of the embodiments above, a proximal end region of the imaging window region abuts the reduced diameter section of the second portion of the hypotube region.

Alternatively or additionally to any of the embodiments above, further comprising a sleeve disposed over the proximal end region of the imaging window region, the reduced diameter section of the second portion of the hypotube region, or both.

An intravascular imaging device is disclosed. The intravascular imaging device comprises: a catheter shaft including a hypotube region, an imaging window region, and a distal end region having a guidewire lumen formed therein; wherein the hypotube region includes a first portion free of slots and a second portion having a plurality of slots formed therein; wherein at least a reduced diameter section of the second portion of the hypotube region has an outer diameter that is less than an outer diameter of the first portion of the hypotube region; wherein a proximal end region of the imaging window region is disposed along the reduced diameter section of the second portion of the hypotube region; and an imaging core disposed within the catheter shaft.

Alternatively or additionally to any of the embodiments above, the reduced diameter section extends along only a distal section of the second portion of the hypotube region.

Alternatively or additionally to any of the embodiments above, the second portion of the hypotube region includes a proximal section having an outer diameter that is substantially equal to the outer diameter of the first portion of the hypotube region.

Alternatively or additionally to any of the embodiments above, the imaging window region includes a distal portion having a first outer diameter and a proximal portion adjacent to the proximal end region having a second outer diameter greater than the first outer diameter.

Alternatively or additionally to any of the embodiments above, further comprising a sleeve disposed along the reduced diameter section and the proximal portion of the imaging window region.

Alternatively or additionally to any of the embodiments above, further comprising a sleeve disposed along the second portion of the hypotube region.

A method for imaging a blood vessel is disclosed. The method comprises: disposing an intravascular imaging device within a blood vessel, the intravascular imaging device comprising: a catheter shaft including a hypotube region, an imaging window region, and a distal end region having a guidewire lumen formed therein, wherein the hypotube region includes a first portion free of slots and a second portion having a plurality of slots formed therein, wherein at least a reduced diameter section of the second portion of the hypotube region has an outer diameter that is less than an outer diameter of the first portion of the hypotube region, wherein the imaging window region is coupled to the reduced diameter section of the second portion of the hypotube region, and an imaging core disposed within the catheter shaft; and translating the imaging core relative to the catheter shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
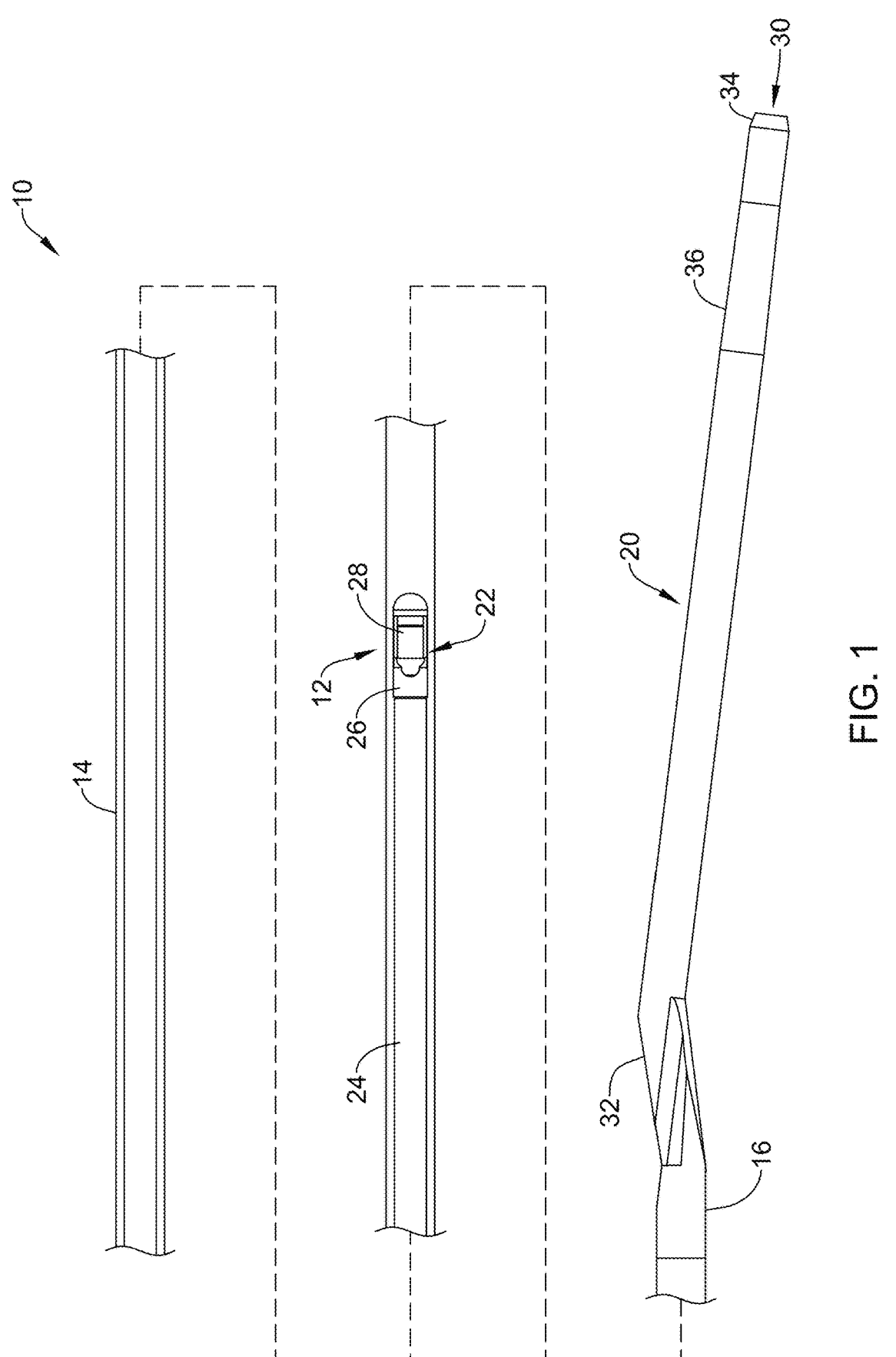
FIG. 1 is a side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of a portion of example medical device 10. In at least some instances, the medical device 10 takes the form of an imaging medical device. For example, the medical device 10 may be an intravascular ultrasound (IVUS) device that may be used to image a blood vessel. In some of these and in other instances, the medical device may be an optical coherence tomography (OCT) imaging device, a near-infrared spectroscopy (NIRS) imaging device, near-infrared fluorescence (NIRF) imaging device, a photoacoustic imaging device, a fluorescence-lifetime imaging device, combinations thereof, and/or the like. The structure/form of the medical device 10 can vary. In some instances, the medical device 10 may include an elongate shaft 12 having a proximal end region 14 and a distal end region 16. A tip member 20 may be coupled to or otherwise disposed adjacent to the distal end region 16. The tip member 20 may include a guidewire lumen 30 having a guidewire exit port 32, an atraumatic distal end 34, one or more radiopaque markers 36, and/or other features. In some embodiments, the tip member 20 may extend at a non-parallel angle to the proximal end region 14 of the elongate shaft 12.

An imaging assembly 22 (e.g., which may sometime be referred to as an imaging core) may be disposed within a lumen of the elongate shaft 12. In general, the imaging assembly 22 may be used to capture/generate images of a blood vessel. In some instances, the medical device may include devices and/or features similar to those disclosed in U.S. Patent Application Pub. No. US 2012/0059241 and U.S. Patent Application Pub. No. US 2017/0164925, the entire disclosures of which are herein incorporated by reference. In at least some instances, the medical device 10 may resemble and/or include features that resemble the OPTI-CROSS™ Imaging Catheter, commercially available from BOSTON SCIENTIFIC, Marlborough, MA.

The imaging assembly 22 may include a drive shaft or cable 24, a housing 26, and an imaging member or transducer 28 coupled to the drive shaft 24 and/or housing 26. In at least some instances, the transducer 28 includes an ultrasound transducer. Other transducers are also contemplated. The transducer 28 may be rotatable and/or axially translatable relative to the elongate shaft 12. For example, the drive shaft 24 may be rotated and/or translated in order to rotate and/or translate the transducer 28 (and the housing 26).

Figure 2:
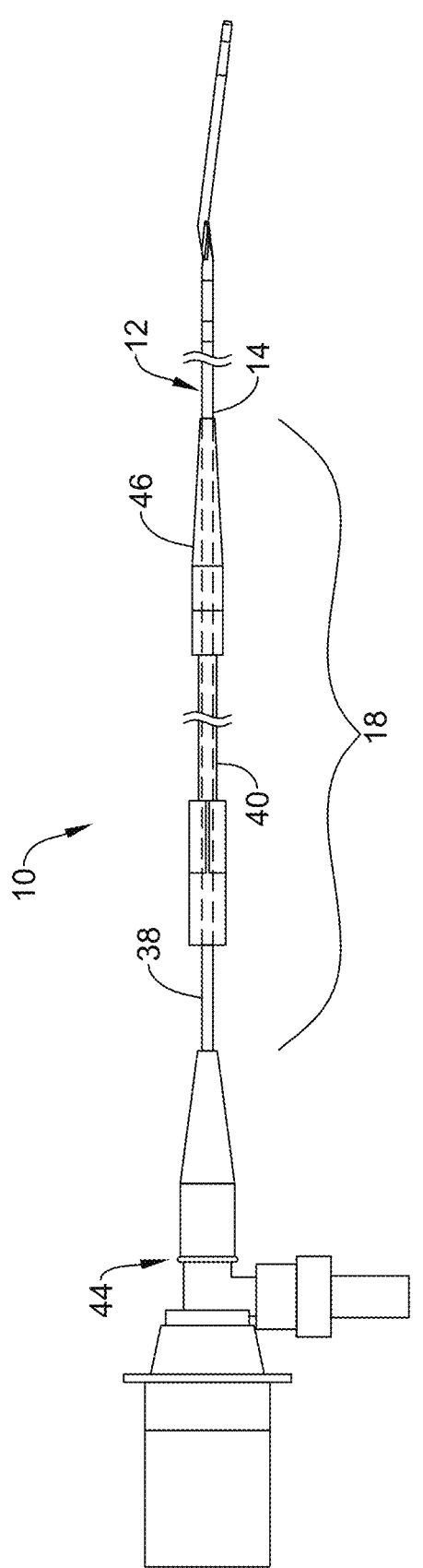
FIG. 2 is a side view of an example medical device.

The proximal end region 14 of the elongate shaft 12 may be coupled to a telescoping assembly 18 as shown in FIG. 2. In general, the telescoping assembly 18 may be configured to allow the medical device operator to move the drive shaft 24 including the imaging assembly 22 proximally and distally within the catheter (e.g., relative to the elongate shaft 12), without having to move the entire catheter within the patient. This allows the catheter operator to easily change the location of the imaging assembly or other medical device within the patient. For example, the telescoping assembly 18 may be actuated to change the location of the imaging assembly 22 within the elongate shaft 12.

The proximal end region 14 of the elongate shaft 12 may be coupled to the telescoping assembly 18. For example, the proximal end region 14 of the elongate shaft 12 may be coupled to a distal hub 46 of the telescoping assembly 18. A proximal hub 44 may be coupled to the telescoping assembly 18 (e.g., at the proximal end of the telescoping assembly 18). The drive shaft 24 (see FIG. 1) may extend through the telescoping assembly 18 and be coupled to and/or otherwise secured to the proximal hub 44.

The telescoping assembly 18 may include a first sheath 38 and a second sheath 40. In some instances, the first sheath 38 may be understood to be an inner telescoping tube 38 and the second sheath 40 may be understood to be an outer telescoping tube 40. Generally, the outer telescoping tube 40 may be disposed over the inner telescoping tube 38. The inner telescoping tube 38 may be coupled to or otherwise secured to the proximal hub 44. The outer telescoping tube 40 may be coupled or otherwise secured to the distal hub 46. The inner telescoping tube 38 may be axially and/or rotatably moveable relative to the outer telescoping tube 40. Because the drive shaft 24 may be secured to the proximal hub 44 and/or the inner telescoping tube 38 and because the elongate shaft 12 may be secured to the distal hub 46, movement of the proximal hub 44 relative to the distal hub 46 results in movement of the inner telescoping tube 38 and the drive shaft 24 relative to the distal hub 46 and/or the elongate shaft 12.

In use, the elongate shaft 12 may be disposed within a target region (e.g., a blood vessel) and the imaging assembly 22 may be translated within the elongate shaft 12 in order to image the blood vessel. It can be appreciated that navigating the elongate shaft 12 through the vasculature toward the target region may include navigating the elongate shaft 12 through a number of tortuous bends and turns. As such, it may be desirable for the elongate shaft 12 to be sufficiently flexible in order to navigate such anatomy. Furthermore, it may be desirable for the elongate shaft 12 to be sufficiently pushable (e.g., in a manner that resists buckling) and be capable of transmitting torque along the length of the elongate shaft 12. Disclosed herein are medical devices (e.g., such as the medical device 10) where the elongate shaft 12 is designed to have a desirable level of flexibility, pushability, torquability, and/or other characteristics.

Figure 3:
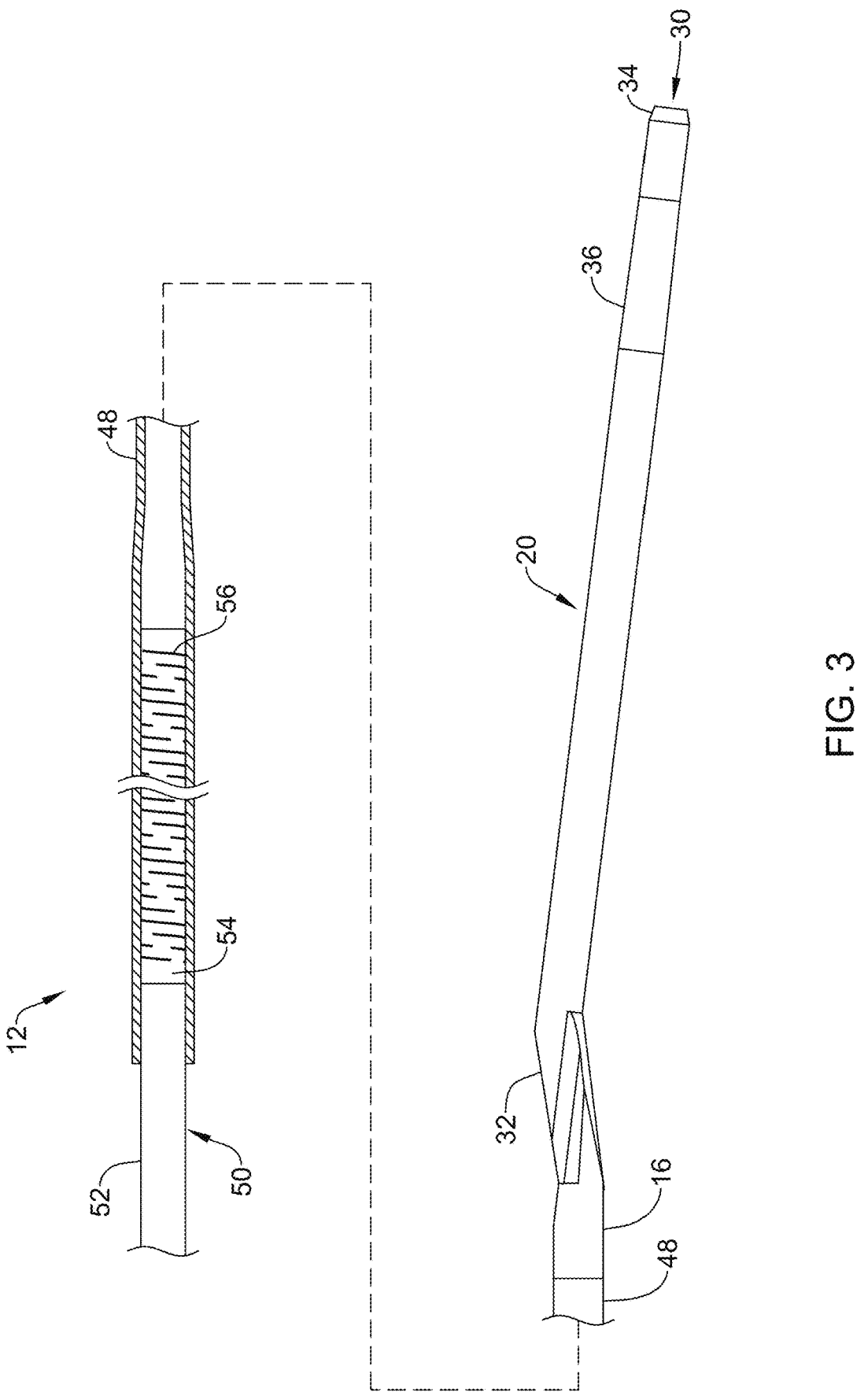
FIG. 3 is a partial cross-sectional side view of a portion of an example medical device.

FIG. 3 illustrate a portion of the elongate shaft 12. As shown and described, the elongate shaft 12 may be an assembly of different parts/regions (e.g., the elongate shaft 12 may be understood to be a catheter shaft or catheter shaft assembly). For example, the elongate shaft 12 may include an imaging window region 48. As the name suggests, the imaging window region 48 is a region of the elongate shaft 12 through which the imaging assembly 22 (e.g., the transducer 28) can image through. While the imaging assembly 22 is not shown in FIG. 3, it can be appreciated that the imaging assembly 22 may be disposed within the elongate shaft 12 in the manner depicted in FIG. 1, for example. The imaging window region 48 may have a distal end that is coupled to and/or otherwise disposed adjacent to the tip member 20. In some instances, the imaging window region 48 extends the full length of the elongate shaft 12 (e.g., the full length proximally from the tip member 20). In other instances, the imaging window region 48 may extend along a portion of the elongate shaft 12. For example, the imaging window region 48 may have a length of about 5-50 cm (1.97-19.7 inches), or about 10-30 cm (3.94-11.8 inches), or about 15-25 cm (5.91-9.84 inches), or about 20-22 cm (7.87-8.66 inches). The imaging window region 48 may be formed from a suitable material such as nylon, nylon-12, polyether block amide, combinations thereof, and/or other suitable materials including those materials disclosed herein.

The elongate shaft 12 may also include a hypotube region 50. The hypotube region 50 may extend proximally from the imaging window region 48 to the distal hub 46. The hypotube region 50 may include a first portion 52 a second portion 54. The first portion 52 may be free of slots. The second portion 54 may have a plurality of slots 56 formed therein. The slots 56 may help to provide a desirable level of flexibility (and/or pushability and/or torqueability) of the elongate shaft 12. Various arrangements and configurations are contemplated for slots 56. For example, in some embodiments, at least some, if not all of the slots 56 are disposed at the same or a similar angle with respect to the longitudinal axis of the hypotube region 50. In some instances, the slots 56 can be disposed at an angle that is perpendicular, or substantially perpendicular, and/or can be characterized as being disposed in a plane that is normal to the longitudinal axis of the hypotube region 50. However, in other instances, the slots 56 can be disposed at an angle that is not perpendicular, and/or can be characterized as being disposed in a plane that is not normal to the longitudinal axis of the hypotube region 50. This may include angled slots 56, slots 56 arranged in a spiral or helical pattern/arrangement, and/or the like. Additionally, a group of one or more slots 56 may be disposed at different angles relative to another group of one or more slots 56. The distribution and/or configuration of the slots 56 can also include, to the extent applicable, any of those disclosed in U.S. Pat. Publication No. US 2004/0181174, the entire disclosure of which is herein incorporated by reference.

The slots 56 can be formed by methods such as micromachining, saw-cutting (e.g., using a diamond grit embedded semiconductor dicing blade), electrical discharge machining, grinding, milling, casting, molding, chemically etching or treating, or other known methods, and the like. In at least some embodiments, the slots 56 may be formed in tubular member using a laser cutting process. The laser cutting process may include a suitable laser and/or laser cutting apparatus. For example, the laser cutting process may utilize a fiber laser. In some embodiments, the slots 56 may have a width of about 0.005-0.04 mm (about 0.0002-0.0016 inches), or about 0.01-0.03 mm (about 0.0004-0.0012 inches), or about 0.02 mm (about 0.0079 inches). The width of the slots 56 may be constant or may be vary along the length of the hypotube region 50. The slots 56 may have an arc length of about 35-75 degrees, or about 40-60 degrees, or about 50 degrees. The spacing between axially-adjacent slots 56 may be about 0.1-4 mm (about 0.0004-0.16 inches), or about 0.2-3 mm (about 0.0008-0.12 inches), or about 0.25-2 mm (about 0.01-0.08 inches). The spacing may be constant or may vary along the length of the hypotube region 50.

In some instances, it may be desirable to improve the bond between the hypotube region 50 and the imaging window region 48 and/or reduce the profile at the bond between the hypotube region 50 and the imaging window region 48. Disclosed herein are catheter shaft and/or intravascular imaging devices (e.g., including catheter shafts) where the bond between the hypotube region and the imaging window is improved and/or the profile is reduced at the bond.

Figures 4, 5:
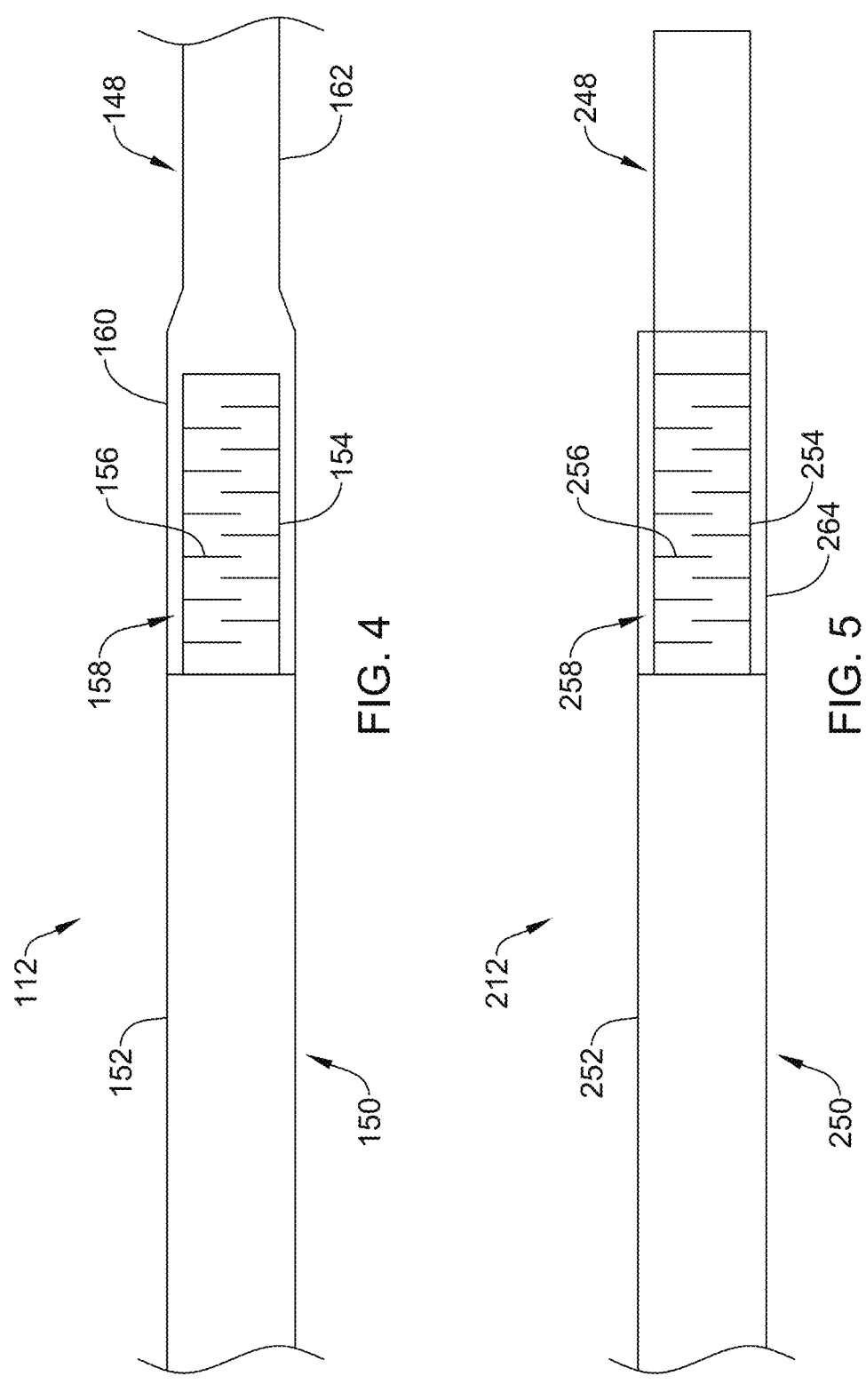
FIG. 4 is a partial cross-sectional side view of a portion of an example medical device.
FIG. 5 is a partial cross-sectional side view of a portion of an example medical device.

FIG. 4 illustrates a portion of the catheter shaft 112 that may be similar in form and function to other catheter shafts disclosed herein. In this example, the catheter shaft 112 may include a hypotube region 150 and an imaging window region 148. The hypotube region 150 may include a first portion 152 and a second portion 154. The first portion 152 may be substantially free of slots or cuts therein. In other words, the first portion 152 may be a solid, uncut hypotube section. The second portion 154 may have a plurality of slots 156 formed therein. The slots 156 may be arranged in a suitable manner including any of those arrangements and/or patterns disclosed herein. In some other instances, a part of the second portion 154 (or the full length of the second portion 154) may be free of slots.

In some instances, the second portion 154 of the hypotube region 150 may have a reduced diameter section 158. The reduced diameter section 158 may have an outer diameter that is less than an outer diameter of the first portion 152 of the hypotube region 150. In at least some instances, the reduced diameter section 158 may have an inner diameter that is substantially equal to the inner diameter of the "non-reduced" part of the second portion 154. For example, the reduced diameter section 158 may be formed by reducing the wall thickness of the second portion 154 (e.g., to thereby form or define the reduced diameter section 158). The same may be true of other reduced diameter sections disclosed herein. The wall thickness of the reduced diameter section 158, for example, may be on the order of about 0.0005-0.003 inches (about 0.0127-0.076 mm), or about 0.001-0.002 inches (about 0.0254-0.0508 mm), or about 0.0015 inches (about 0.0381 inches). The reduced diameter section 158 may help to improve the integrity of the bond between the imaging window region 148 and/or help to manage the outer diameter of the catheter shaft 112. In some instances, the reduced diameter section 158 may extend along the full length of the second portion 154 of the hypotube region 150. In other instances, the reduced diameter section 158 may extend along a portion of the length of the second portion 154 of the hypotube region 150.

The imaging window region 148 may include a proximal portion 160 and a distal portion 162. The proximal portion 160 may have an outer diameter that is larger than the distal portion 162. In some instances, the proximal portion 160 may be disposed along and/or overlap with the reduced diameter section 158 of the second portion 154 of the hypotube region 150. Because, for example, the reduced diameter section 158 has a reduced diameter relative to first portion 152 of the hypotube region 150, the proximal portion 160 may fit over the reduced diameter section 158. This may include engaging and/or abutting the first portion 152 of the hypotube region 150. In some instances, the outer diameter proximal portion 160 may be substantially equal to the first portion 152 of the hypotube region 150. This may allow the catheter shaft 112 to have a substantially constant outer diameter across the joint/junction of the proximal portion 160 of the imaging window region 148 and the first portion 152 of the hypotube region 150.

FIG. 5 illustrates a portion of the catheter shaft 212 that may be similar in form and function to other catheter shafts disclosed herein. In this example, the catheter shaft 212 may include a hypotube region 250 and an imaging window region 248. The hypotube region 250 may include a first portion 252 and a second portion 254. The first portion 252 may be substantially free of slots or cuts therein. The second portion 254 may have a plurality of slots 256 formed therein. The slots 256 may be arranged in a suitable manner including any of those arrangements and/or patterns disclosed herein. In some other instances, a part of the second portion 254 (or the full length of the second portion 254) may be free of slots.

In some instances, the second portion 254 of the hypotube region 250 may have a reduced diameter section 258. The reduced diameter section 258 may have an outer diameter that is less than an outer diameter of the first portion 252 of the hypotube region 250. The reduced diameter section 258 may help to improve the integrity of the bond between the imaging window region 248 and/or help to manage the outer diameter of the catheter shaft 212. In some instances, the reduced diameter section 258 may extend along the full length of the second portion 254 of the hypotube region 250. In other instances, the reduced diameter section 258 may extend along a portion of the length of the second portion 254 of the hypotube region 250. The imaging window region 248 may engage and/or abut the reduced diameter section 258.

A sleeve 264 may be disposed over the reduced diameter section 258 of the second portion 254 of the hypotube region 250. The sleeve 264 (and/or other sleeves disclosed herein) may include a suitable material such as nylon, nylon-12, polyether block amide, high density polyethylene, low density polyethylene, polypropylene, polytetrafluoroethylene, other suitable materials including those disclosed herein, combinations thereof, and/or the like. In general, suitable materials for the sleeve 264 may include acoustically compatible materials. Such materials may have a flexural moduli ranging from about 0.5-3.0 GPa and/or have an acoustic impedance ranging from about 1.0-3.0 MRy. These are just examples. In some instances, the sleeve 264 may at least partially overlap and/or be disposed along both the reduced diameter section 258 and the imaging window region 248. The sleeve 264 may abut the first portion 252 of the hypotube region 250. In some instances, the sleeve 264 may have an outer diameter that is substantially equal to the first portion 252 of the hypotube region 250. This may allow the catheter shaft 212 to have a substantially constant outer diameter across the joint/junction of the first portion 252 of the hypotube region 250 and the sleeve 264.

Figures 6, 7:
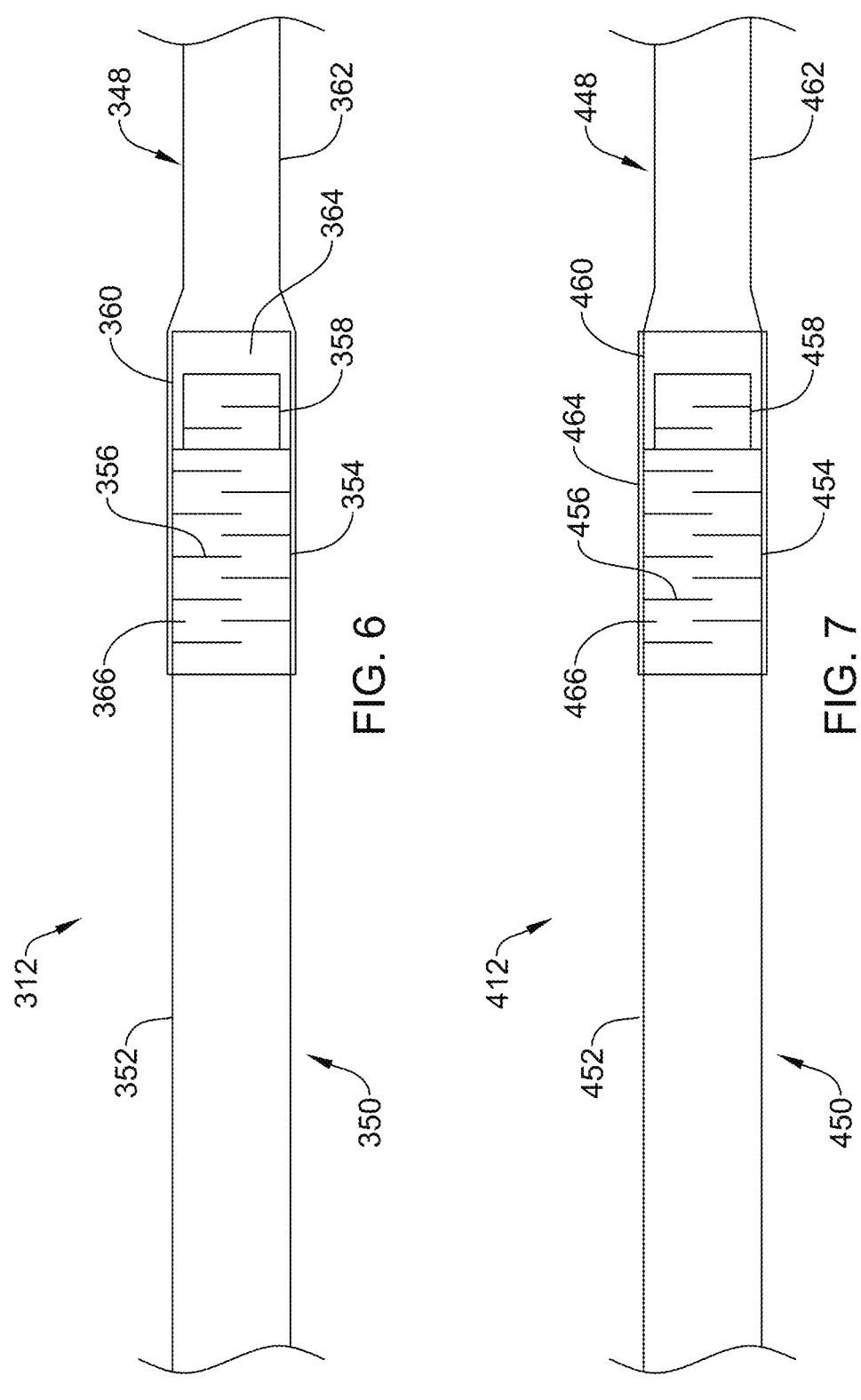
FIG. 6 is a partial cross-sectional side view of a portion of an example medical device.
FIG. 7 is a partial cross-sectional side view of a portion of an example medical device.

FIG. 6 illustrates a portion of the catheter shaft 312 that may be similar in form and function to other catheter shafts disclosed herein. In this example, the catheter shaft 312 may include a hypotube region 350 and an imaging window region 348. The hypotube region 350 may include a first portion 352 and a second portion 354. The first portion 352 may be substantially free of slots or cuts therein. The second portion 354 may have a plurality of slots 356 formed therein. The slots 356 may be arranged in a suitable manner including any of those arrangements and/or patterns disclosed herein.

The second portion 354 of the hypotube region 350 may have a reduced diameter section 358. The reduced diameter section 358 may have an outer diameter that is less than an outer diameter of the first portion 352 of the hypotube region 350. In some instances, the reduced diameter section 358 may extend along the full length of the second portion 354 of the hypotube region 350. In other instances, the reduced diameter section 358 may extend along a portion of the length of the second portion 354 of the hypotube region 350. For example, the second portion 354 of the hypotube region 350 may include a proximal portion 366. The proximal portion 366 may have an outer diameter that is greater than reduced diameter section 358. In some of these and in other instances, the proximal portion 366 may have an outer diameter that is substantially equal to the outer diameter of the first portion 352 of the hypotube region 350. In some instances, a sleeve 364 may be disposed along the reduced diameter section 358. The sleeve 364 may abut the proximal portion 366.

The imaging window region 348 may include a proximal portion 360 and a distal portion 362. The proximal portion 360 may have an outer diameter that is larger than the distal portion 362. In some instances, the proximal portion 360 may be disposed along and/or overlap with the reduced diameter section 358 of the second portion 354 of the hypotube region 350. This may also include the proximal portion 360 being disposed along and/or overlapping with the proximal portion 366.

FIG. 7 illustrates a portion of the catheter shaft 412 that may be similar in form and function to other catheter shafts disclosed herein. In this example, the catheter shaft 412 may include a hypotube region 450 and an imaging window region 448. The hypotube region 450 may include a first portion 452 and a second portion 454. The first portion 452 may be substantially free of slots or cuts therein. The second portion 454 may have a plurality of slots 456 formed therein. The slots 456 may be arranged in a suitable manner including any of those arrangements and/or patterns disclosed herein.

The second portion 454 of the hypotube region 450 may have a reduced diameter section 458. The reduced diameter section 458 may have an outer diameter that is less than an outer diameter of the first portion 452 of the hypotube region 450. In some instances, the reduced diameter section 458 may extend along the full length of the second portion 454 of the hypotube region 450. In other instances, the reduced diameter section 458 may extend along a portion of the length of the second portion 454 of the hypotube region 450. For example, the second portion 454 of the hypotube region 450 may include a proximal portion 466.

In some instances, a sleeve 464 may be disposed along the reduced diameter section 458. The sleeve 464 may at least partially overlap and/or be disposed along both the reduced diameter section 458 and the proximal portion 466. The sleeve 464 may extend toward the first portion 452 of the hypotube region 450 and, in some instances, may extend proximally of the distal end of the first portion 452 of the hypotube region 450. In some instances, the sleeve 464 may have an outer diameter that is greater than the first portion 452 of the hypotube region 450.

The imaging window region 448 may include a proximal portion 460 and a distal portion 462. The proximal portion 460 may have an outer diameter that is larger than the distal portion 462. In some instances, the proximal portion 460 may be disposed along and/or overlap with the reduced diameter section 458 of the second portion 454 of the hypotube region 450. This may also include the proximal portion 460 abutting the proximal portion 466.

Figures 8, 9:
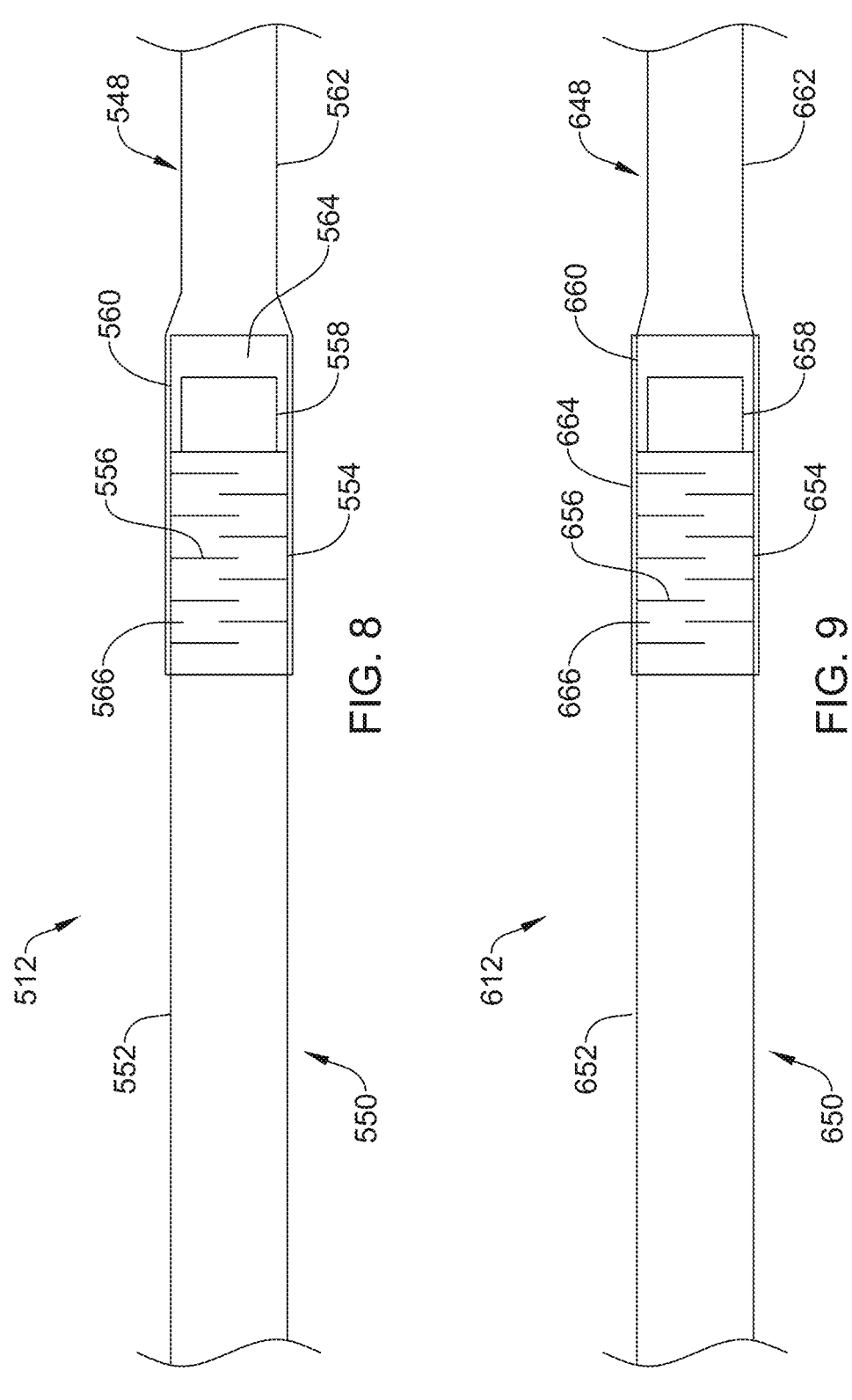
FIG. 8 is a partial cross-sectional side view of a portion of an example medical device.
FIG. 9 is a partial cross-sectional side view of a portion of an example medical device.

FIG. 8 illustrates a portion of the catheter shaft 512 that may be similar in form and function to other catheter shafts disclosed herein. In this example, the catheter shaft 512 may include a hypotube region 550 and an imaging window region 548. The hypotube region 550 may include a first portion 552 and a second portion 554. The first portion 552 may be substantially free of slots or cuts therein. The second portion 554 may have a plurality of slots 556 formed therein. The slots 556 may be arranged in a suitable manner including any of those arrangements and/or patterns disclosed herein.

The second portion 554 of the hypotube region 550 may have a reduced diameter section 558. The reduced diameter section 558 may have an outer diameter that is less than an outer diameter of the first portion 552 of the hypotube region

550. In some instances, the reduced diameter section 558 may extend along the full length of the second portion 554 of the hypotube region 550. In other instances, the reduced diameter section 558 may extend along a portion of the length of the second portion 554 of the hypotube region 550. For example, the second portion 554 of the hypotube region 550 may include a proximal portion 566. The proximal portion 566 may have an outer diameter that is greater than reduced diameter section 558. In some of these and in other instances, the proximal portion 566 may have an outer diameter that is substantially equal to the outer diameter of the first portion 552 of the hypotube region 550. In some instances, a sleeve 564 may be disposed along the reduced diameter section 558. The sleeve 564 may abut the proximal portion 566.

The arrangement of the slots 556 along the second portion 554 may vary. For example, in some instances the slots 556 may extend along substantially the full length of the second portion 554 of the hypotube region 550. In other words, both the proximal portion 566 and the reduced diameter section 558 may include the slots 556. In other instances, the reduced diameter section 558 (and/or a portion thereof) may be free of slots. In some of these and in other instances, a part or all of the proximal portion 556 may be free of slots.

The imaging window region 548 may include a proximal portion 560 and a distal portion 562. The proximal portion 560 may have an outer diameter that is larger than the distal portion 562. In some instances, the proximal portion 560 may be disposed along and/or overlap with the reduced diameter section 558 of the second portion 554 of the hypotube region 550. This may also include the proximal portion 560 being disposed along and/or overlapping with the proximal portion 566.

FIG. 9 illustrates a portion of the catheter shaft 612 that may be similar in form and function to other catheter shafts disclosed herein. In this example, the catheter shaft 612 may include a hypotube region 650 and an imaging window region 648. The hypotube region 650 may include a first portion 652 and a second portion 654. The first portion 652 may be substantially free of slots or cuts therein. The second portion 654 may have a plurality of slots 656 formed therein. The slots 656 may be arranged in a suitable manner including any of those arrangements and/or patterns disclosed herein.

The second portion 654 of the hypotube region 650 may have a reduced diameter section 658. The reduced diameter section 658 may have an outer diameter that is less than an outer diameter of the first portion 652 of the hypotube region 650. In some instances, the reduced diameter section 658 may extend along the full length of the second portion 654 of the hypotube region 650. In other instances, the reduced diameter section 658 may extend along a portion of the length of the second portion 654 of the hypotube region 650. For example, the second portion 654 of the hypotube region 650 may include a proximal portion 666.

The arrangement of the slots 656 along the second portion 654 may vary. For example, in some instances the slots 656 may extend along substantially the full length of the second portion 654 of the hypotube region 650. In other words, both the proximal portion 666 and the reduced diameter section 658 may include the slots 656. In other instances, the reduced diameter section 658 (and/or a portion thereof) may be free of slots. In some of these and in other instances, a part or all of the proximal portion 656 may be free of slots.

In some instances, a sleeve 664 may be disposed along the reduced diameter section 658. The sleeve 664 may at least partially overlap and/or be disposed along both the reduced diameter section 658 and the proximal portion 666. The sleeve 664 may extend toward the first portion 652 of the hypotube region 650 and, in some instances, may extend proximally of the distal end of the first portion 652 of the hypotube region 650. In some instances, the sleeve 664 may have an outer diameter that is greater than the first portion 652 of the hypotube region 650.

The imaging window region 648 may include a proximal portion 660 and a distal portion 662. The proximal portion 660 may have an outer diameter that is larger than the distal portion 662. In some instances, the proximal portion 660 may be disposed along and/or overlap with the reduced diameter section 658 of the second portion 654 of the hypotube region 650. This may also include the proximal portion 660 abutting the proximal portion 666.

The materials that can be used for the various components of the medical device 10 (and/or other devices disclosed herein) and the various tubular members disclosed herein may include those commonly associated with medical devices. For simplicity purposes, the following discussion refers to the elongate shaft 12 and other components of the medical device 10. However, this is not intended to limit the devices and methods described herein, as the discussion may be applied to other similar tubular members and/or components of tubular members or devices disclosed herein.

The elongate shaft 12 and/or other components of the medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the medical device 10. For example, the medical device 10, or portions thereof, may be made of a material that does not substantially distort the image and create substantial artifacts (e.g., gaps in the image). Certain ferromagnetic materials, for example, may not be suitable because they may create artifacts in an MRI image. The medical device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular imaging device, comprising:
a catheter shaft including a hypotube region, an imaging window region, and a distal end region having a guidewire lumen formed therein;
wherein the hypotube region includes a first portion free of slots and a second portion having a plurality of slots formed therein;

wherein at least a reduced diameter section of the second portion of the hypotube region has an outer diameter that is less than an outer diameter of the first portion of the hypotube region;

wherein the imaging window region overlaps with and is coupled to the reduced diameter section of the second portion of the hypotube region; and an imaging core disposed within the catheter shaft.

2. The intravascular imaging device of claim 1, wherein the imaging core is translatable within the catheter shaft.

3. The intravascular imaging device of claim 1, wherein the imaging core includes an ultrasound transducer.

4. The intravascular imaging device of claim 1, wherein the imaging core includes an optical coherence tomography imaging device.

5. The intravascular imaging device of claim 1, wherein the reduced diameter section extends along substantially the full length of the second portion of the hypotube region.

6. The intravascular imaging device of claim 1, wherein the reduced diameter section extends along only a distal section of the second portion of the hypotube region.

7. The intravascular imaging device of claim 6, wherein the second portion of the hypotube region includes a proximal section having an outer diameter that is substantially equal to the outer diameter of the first portion of the hypotube region.

8. The intravascular imaging device of claim 1, wherein the imaging window region includes a distal portion having a first outer diameter and a proximal portion having a second outer diameter greater than the first outer diameter.

9. The intravascular imaging device of claim 8, wherein the proximal portion of the imaging window region is disposed along the reduced diameter section of the second portion of the hypotube region.

10. The intravascular imaging device of claim 8, further comprising a sleeve disposed along the reduced diameter section of the proximal portion of the imaging window region.

11. The intravascular imaging device of claim 8, further comprising a sleeve disposed along the second portion of the hypotube region.

12. The intravascular imaging device of claim 1, wherein a proximal end region of the imaging window region abuts the reduced diameter section of the second portion of the hypotube region.

13. The intravascular imaging device of claim 12, further comprising a sleeve disposed over the proximal end region of the imaging window region, the reduced diameter section of the second portion of the hypotube region, or both.

14. An intravascular imaging device, comprising:
a catheter shaft including a hypotube region, an imaging window region, and a distal end region having a guidewire lumen formed therein;

wherein the hypotube region includes a first portion free of slots and a second portion having a plurality of slots formed therein;

wherein the first portion has a first outer diameter;

wherein the second portion has a second outer diameter less than the first outer diameter;

wherein the hypotube region includes a stepped transition between the first outer diameter and the second outer diameter;

wherein a proximal end region of the imaging window region is disposed along the reduced diameter section of the second portion of the hypotube region; and an imaging core disposed within the catheter shaft.

15. The intravascular imaging device of claim 14, wherein the reduced diameter section extends along only a distal section of the second portion of the hypotube region.

16. The intravascular imaging device of claim 15, wherein the second portion of the hypotube region includes a proximal section having an outer diameter that is substantially equal to the outer diameter of the first portion of the hypotube region.

17. The intravascular imaging device of claim 14, wherein the imaging window region includes a distal portion having a first outer diameter and a proximal portion adjacent to the proximal end region having a second outer diameter greater than the first outer diameter.

18. The intravascular imaging device of claim 17, further comprising a sleeve disposed along the reduced diameter section and the proximal portion of the imaging window region.

19. The intravascular imaging device of claim 17, further comprising a sleeve disposed along the second portion of the hypotube region.

20. A method for imaging a blood vessel, the method comprising:
disposing an intravascular imaging device within a blood vessel, the intravascular imaging device comprising:
a catheter shaft including a hypotube region, an imaging window region, and a distal end region having a guidewire lumen formed therein,
wherein the hypotube region includes a first portion free of slots and a second portion having a plurality of slots formed therein,
wherein at least a reduced diameter section of the second portion of the hypotube region has an outer diameter that is less than an outer diameter of the first portion of the hypotube region,
wherein the imaging window region overlaps with and is coupled to the reduced diameter section of the second portion of the hypotube region, and
an imaging core disposed within the catheter shaft; and
translating the imaging core relative to the catheter shaft.

* * * * *